United States Patent [19]

Jones et al.

[11] Patent Number: 5,037,657

[45] Date of Patent: Aug. 6, 1991

[54] EFFERVESCENT ACETYSALICYLIC ACID

[75] Inventors: Stephen K. Jones, Wantirna South; Peter D. Wilson, Surrey Hills, both of Australia

[73] Assignee: Nicholas Kiwi Pty Limited, Victoria, Australia

[21] Appl. No.: 491,739

[22] Filed: Mar. 12, 1990

Related U.S. Application Data

[63] Continuation of Ser. No. 86,089, Sep. 15, 1987, abandoned.

[30] Foreign Application Priority Data

Oct. 15, 1985 [GB] United Kingdom ................ 8525348
Oct. 14, 1986 [AU] Australia ......... PCT/AU86/00304

[51] Int. Cl.$^5$ ............................................. A61K 9/46
[52] U.S. Cl. .................................. 424/466; 424/479; 424/493; 424/717
[58] Field of Search ................... 424/44, 466; 106/210

[56] References Cited

U.S. PATENT DOCUMENTS

| 3,882,228 | 5/1975 | Boncey et al. | 424/44 |
| 3,887,700 | 6/1975 | Boncey et al. | 424/44 |
| 4,079,132 | 3/1978 | Lin et al. | 424/230 |
| 4,369,308 | 1/1983 | Trubiano | 106/210 |
| 4,551,177 | 11/1985 | Trubiano et al. | 106/210 |
| 4,650,669 | 3/1987 | Alexander | 424/44 |

FOREIGN PATENT DOCUMENTS

| 1274797 | 5/1972 | United Kingdom . |  |
| 1275086 | 5/1972 | United Kingdom . |  |
| 1287475 | 8/1972 | United Kingdom . |  |
| 1473315 | 5/1977 | United Kingdom | 424/44 |

*Primary Examiner*—Thurman K. Page
*Assistant Examiner*—E. Webman
*Attorney, Agent, or Firm*—Nixon & Vanderhye

[57] ABSTRACT

The rate of disintegration and/or dissolution of effervescent acetylsalicylic acid tablets obtained by direct compression of a dry powder mixture is surprisingly increased by incorporating in said mixture powdered dextrose and/or sucrose. Preferably, spray-crystallized dextrose is used.

7 Claims, No Drawings

EFFERVESCENT ACETYSALICYLIC ACID

This is a continuation of application Ser. No. 07/086,089, filed Sept. 15, 1987, now abandoned.

The present invention relates to effervescent acetylsalicylic acid tablets.

Effervescent tablets contain an effervescent couple consisting of a base component and an acid component, which components react in the presence of water to generate a gas. Said gas generation usually is required either to provide an aerated palatable drink and/or to assist dispersion and/or dissolution of an active tablet component having, for example, sterilising or pharmacological activity. Usually, the base component comprises an alkali metal or alkaline earth metal carbonate or bicarbonate and the acid component comprises an aliphatic carboxylic acid, whereby carbon dioxide is generated on addition to water.

Effervescent tablets usually are prepared either by a granulation method or by a direct compression method. In granulation methods, moist granules of the components are first formed and are subsequently screened, dried and lubricated before compression into tablets. The moisture can be provided by use of a hydrated component and subsequently heating a dry mixture containing that component to release the water of crystallization Alternatively, steam or water can be sprayed or injected into an essentially anhydrous mixture. The water can be in the form of a solution of a binding material such as acacia, gelatine, lactose or sugar. In the direct compression method, a dry powder mixture is directly compressed on a tablet press to form tablets. Although the direct compression method is more cost effective in terms of both labour and equipment, it is of less general application than the granulation process and often provides effervescent tablets of inferior properties to those obtained by the granulation process.

Acetylsalicylic acid is particularly well suited to formulation by direct compression into effervescent tablet form. In particular, acetylsalicylic acid crystals provide adequate lubricating properties so that directly compressible effervescent formulations containing acetylsalicylic acid at effective dose levels usually do not require additional lubricant. Further, on addition of the tablet to water, the acetylsalicylic acid forms a water-soluble salt with the cation derived from the base component of the effervescent couple thereby converting the acetylsalicylic acid from a poorly soluble into a readily soluble form.

Effervescent acetylsalicylic acid tablets normally comprise essentially acetylsalicylic acid, sodium bicarbonate and citric acid. In order to obtain a substantially completely clear solution within an acceptable time (1-2 minutes) following addition of the tablet to water, effervescent acetylsalicylic acid tablets of conventional formulation require a substantial quantity of effervescent couple. Typically, a conventional effervescent acetylsalicylic acid tablet containing 300 mg acetylsalicylic acid contains about 2.5 g effervescent couple. The resultant high concentration of sodium ions in the carbonated solution is a significant disadvantage of such tablets. U.K. Patent No. 1287475 teaches that the quantity of effervescent couple in effervescent acetylsalicylic acid tablets can be substantially reduced by using acetylsalicylic acid particles coated with a specific class of water-soluble coating material. This material has a melting point of at least 105° C. and consists essentially of low molecular weight amino acid, sugar and/or sugar alcohol. The preferred coating materials are mannitol, inositol and glycine. The use of such coated acetylsalicylic acid particles permits a reduction of more than half in the quantity of effervescent couple required to provide a clear solution within about 1 minute of addition to water.

Effervescent tablets present two essentially conflicting problems distinct from those encountered with non-effervescent tablets. First, effervescent tablets must contain no water because even trace amounts of water can activate the effervescent couple during storage and thereby decompose the tablet prior to use. Second, the effervescent tablet is required to disintegrate and/or dissolve rapidly upon addition to water. Accordingly, consideration must be given to the effects upon both stability and disintegration/dissolution of introducing into an effervescent tablet a component in addition to the effervescent couple and the active component, if any. Binders, diluents, lubricants and other excipients are used extensively in conventional non-effervescent tablets. However, their use in effervescent tablets is limited by their affect on stability and, especially, disintegration/dissolution of the tablets. In general terms, such additives hinder disintegration/dissolution even if they have good water-solubility and are anhydrous. With some exceptions, notably effervescent tablets containing acetylsalicylic acid, a lubricant such as magnesium stearate is required to facilitate tableting. Binders are often required, especially in granulation methods, but are used in minimal amounts required for satisfactory tablet formation. Similarly sweetening and flavouring agents are used only when necessary to provide a palatable aerated suspension or solution. Diluents usually are not required because of the bulk provided by the effervescent couple. Usually, effervescent acetylsalicylic acid tablets do not contain binders, diluents, lubricants or other excipients except for sweetening and flavouring agents to provide a palatable carbonated solution.

As mentioned previously, the use of binders in effervescent tablets is to be avoided as far as possible. Pharmaceutical Dosage Forms: Tablets, Volume 1, 1980 (H. A. Liebermann and L. Lachman) states in the paragraph bridging pages 229 and 230 as follows:

"Compared to their use in conventional tablets, the use of binders in effervescent tablet formulations is limited, not because the binders are unnecessary, but because of the two way action of the binders themselves. The use of any binder, even one that is water soluble, will retard the disintegration of an effervescent tablet. In granulations which require a binder for tableting, a proper balance must be chosen between granule cohesiveness and desired tablet disintegration. Binders such as the natural and cellulose gums, gelatine, and starch paste are generally not useful due to their slow solubility or high residual water content. Dry binders such as lactose, dextrose and mannitol can be used but are often not effective in the low concentrations normally permissible in effervescent tablets due to their disintegration-hindering properties as well as weight/volume constraints. Most effervescent tablets are composed primarily of ingredients needed to produce effervescence or to carry out the function of the tablet. Usually there is little room for excipients, which are needed in large concentrations to be effective. Polyvinylpyrrolidone (PVP) is an effective effervescent tablet binder."

Subsequently at page 237 when referring to the problem of granulations sticking to the wall of the tablet dye, it is stated that:

"Modifications in the binder and lubricant systems contained in the formulation can solve these problems; but as previously mentioned the effects of both binders and lubricants are detrimental to tablet disintegration and, in the case of lubricants, the hardness of the tablets".

In the context of the present invention, it is relevant to note that sugars and sugar alcohols, including sucrose and dextrose, have been proposed for use as binders and/or sweetening agents in effervescent tablets (see, for example, GB 1270781, 1274797, GB 1287475, U.S. Pat. No. 2,854,377 and U.S. Pat. No. 3,882,228, and Pharmaceutical Dosage Forms: Tablets (supra)). The use of mannitol or lactose as an inert extender in effervescent acetylsalicylic acid tablets is taught in GB 2148117. In these tablets, the effervescent couple comprises acid crystals having a coating containing calcium carbonate in order to reduce the sodium ion content of the solution resulting from dissolution of the tablets in water. Preferably, the crystals also have a second potassium hydrogen carbonate-containing layer and a third fumaric acid containing layer. However, the prior art clearly teaches that polyvinylpyrrolidone (PVP) is preferred to sugars or sugar alcohols as a binding agent for effervescent tablets and that the use of binding agents hinders disintegration/dissolution of the tablets. Further, as mentioned previously, effervescent acetylsalicylic acid tablets do not require binders or lubricants.

Spray-crystallized dextrose powder is available under the Trade Marks "EMDEX" and "TAB BASE" as a vehicle for the manufacture of directly compressed non-effervescent tablets. The vehicle serves as a binder and diluent in the tablet formulation. It has been reported that non-effervescent directly compressed tablets using this vehicle disintegrate by dissolution rather than by disruption of interparticulate bonds. The disintegration is reported to be more rapid than occurs when using conventional direct compression vehicles such as anhydrous or spray-dried lactose or microcrystalline cellulose. Its use in both chewable and non-chewable tablets has been proposed. However, it has not, to the best of the Applicant's knowledge, been publicly proposed to use the vehicle in effervescent tablets. As reported above, the use of a direct compression vehicle in an effervescent tablet is contra-indicated. The presence of the effervescent couple precludes and/or renders unnecessary the use of a diluent in acetylsalicylic acid effervescent tablets. Binders are not used unless, and only in such amount as, required to produce a satisfactory tablet. The art teaches that even water soluble binders hinder disintegration/dissolution of an effervescent tablet.

The spray-crystallized dextrose available under the Trade Marks EMDEX and TAB BASE is composed almost entirely of dextrose microcrystals in the form of free-flowing porous spheres, the remainder being maltose and higher saccharides. The dextrose equivalent is at least 95, typically 97, and the particle size predominately (at least 60%) in the range 20 to 100 mesh (BSS). A typical particle size distribution is as follows:

| Mesh | Percent |
| --- | --- |
| 0–30 | 9.0 |
| 30–60 | 57.8 |
| 60–100 | 23.2 |
| Greater than 100 | 10.0 |

The bulk densities are 0.58 g/ml (TAB BASE) and 0.73 g/ml (EMDEX) and the tapped densities are 0.68 g/ml (TAB BASE) and 0.82 g/ml (EMDEX).

It has now surprisingly been found that the dissolution time of effervescent acetylsalicylic acid tablets produced by direct compression is reduced by the incorporation of powdered sucrose or, preferably, dextrose in the powder mixture prior to compression without significant reduction in tablet stability.

Accordingly, a first aspect of the present invention provides the use of powdered dextrose and/or sucrose as a disintegrant and/or dissolution aid in an effervescent acetylsalicylic acid tablet obtained by direct compression of a dry powder mixture.

A second aspect of the present invention provides a method of increasing the rate of disintegration and/or dissolution of an effervescent acetylsalicylic acid tablet obtained by direct compression of a dry powder mixture which comprises incorporating in said mixture powdered dextrose and/or sucrose.

According to a third aspect of the present invention, there is provided an effervescent acetylsalicylic acid tablet obtained by direct compression of a directly compressible dry powder mixture admixed with powdered dextrose and/or sucrose in an amount sufficient to increase the rate of disintegration and/or dissolution of the tablet compared with said directly compressed dry powder mixture.

Usually, the dextrose and/or sucrose will be used in an amount of 10 to 40%, preferably 15 to 30%, by weight based upon the combined weights of the other components of the tablet. These ranges correspond respectively to 10 to 30% and 15 to 25% by weight of the total tablet weight.

It is preferred that the dextrose and/or sucrose used is agglomerated or, especially, spray-crystallized. Presently, it is preferred to use dextrose, especially in the form of a dextrate (ie. a mixture of saccharides containing the equivalent of 93 to 99% dextrose). The presently most preferred dextrose is spray-crystallized dextrose such as that available under the Trade Marks EMDEX and TAB BASE.

It has been found that effervescent tablets incorporating spray-crystallized dextrose maintain faster dissolution times compared with otherwise identical tablets containing alternative sugars or sugar alcohols, which other tablets may dissolve quicker initially but dissolve more slowly after storage.

It is preferred that the base component of the effervescent couple is sodium bicarbonate or, especially, a mixture of a major proportion of sodium bicarbonate with a minor proportion of sodium carbonate. The sodium carbonate suitably contributes 5 to 25% by weight of said bicarbonate/carbonate mixture.

When a formulation of reduced, or no, sodium ion content is required, said sodium salts usually will be partly, or wholly, replaced by the corresponding potassium salts.

The presently preferred acid component is citric acid or a salt thereof. It is particularly preferred to use either citric acid per se or a mixture of citric acid with mono-, di- and/or tri- sodium citrate.

As mentioned previously, the invention has particular application to effervescent acetylsalicylic acid tablets in which the acetylsalicylic acid is in the form of coated acetylsalicylic acid particles as disclosed in U.K. Patent No. 1287475. Such coated particles are referred to in the Examples hereinafter as 'coated ASA'.

The invention is illustrated in the following non-limiting Examples. In all cases dissolution times were determined by adding two tablets to 100 ml water at 20° C. and recording the time taken for both tablets to completely dissolve to a clear solution. The abbreviation "kp" means kilopond, which is a metric measurement of tablet hardness. 1 kp equals 1 kilogramme-force equals 9.8 Newtons.

EXAMPLE 1

Effervescent acetylsalicylic acid tablets were produced by direct compression of dry powder mixtures of the following formulations:

| (A) | Coated ASA | 350 mg |
|---|---|---|
| | NaHCO$_3$/Na$_2$CO$_3$ | 460 |
| | Citric acid/tri-sodium citrate mixture | 435 mg |

(B) Formulation A above with addition of 200 mg TAB BASE (spray crystallized dextrose).
(C) Formulation A above with addition of 400 mg TAB BASE.
(D) Formulation A above with addition of 200 mg mannitol.
(E) Formulation A above with addition of 400 mg mannitol.
(F) Formulation A above with addition of 200 mg fructose.
(G) Formulation A above with addition of 400 mg fructose.

With the exception of Formulation G, the tablets were compressed to a hardness of 7 to 9 kp. In the case of tablets of Formulation G, the hardness was 7 to 11 kp.

The initial dissolution times for the tablets are set forth in Table 1 below:

TABLE 1

| Formulation | Average Dissolution Time (Range) Secs |
|---|---|
| A | 101 (86–115) |
| B | 68 (60–82) |
| C | 54 (44–68) |
| D | 73 (58–89) |
| E | 51 (47–55) |
| F | 101 (92–107) |
| G | 153 (139–174) |

It will be noted from Table 1 that the addition of 200 mg or 400 mg of spray-crystallized dextrose or of mannitol caused a substantial reduction in initial dissolution time. The addition of 200 mg fructose did not, reduce the average initial dissolution time but did reduce the range over which dissolution varied from tablet to tablet. However, addition of 400 mg fructose substantially increased the initial dissolution time.

It was found that, although the addition of 400 mg mannitol gave quicker dissolution initially than the addition of 400 mg dextrose, the dextrose-containing tablets had quicker dissolution times after storage. For example, after 4 weeks at 20° C., the mannitol-containing tablets (Formulation E) dissolved in 87 secs compared with 61 secs for the dextrose-containing tablets (Formulation C). Similarly, after 4 weeks storage at 40° C., the mannitol tablets took 105 secs to dissolve compared with 77 secs for the dextrose tablets. The dissolution times after storage for the time and at the temperature specified are set forth in Table 2 below:

TABLE 2

| Time | Initially | 2 weeks | 4 weeks | | |
|---|---|---|---|---|---|
| Temperature | — | 50° C. | 20° C. | 40° C. | 50° C. |
| Formulation | | Average Dissolution Time (secs) | | | |
| A | 101 | 203 | ND | ND | NS |
| B | 68 | 91 | ND | ND | 99 |
| C | 54 | ND | 61 | 77 | 73 |
| D | 73 | 141 | ND | ND | 156 |
| E | 51 | 113 | 87 | 105 | NS |
| F | 101 | 169 | ND | ND | NS |
| G | 153 | ND | ND | ND | ND |

ND = not determined
NS = not stable

Additional batches of tablets for Formulations A and C (hardness 7–9 kp) were subjected to further testing and the following results obtained:

TABLE 3

| Formulation | | Average Dissolution Time (range) (secs) | |
|---|---|---|---|
| Time (weeks) | Temperature (°C.) | A | C |
| Initially | | 81 | 66 |
| 2 | 40° | 135 | 89 (73–105) |
| 2 | 50° | 145 | 93 (91–95) |
| 4 | 20° | (130–160) | 80 (75–85) |
| 4 | 40° | (140–160) | 95 (80–115) |
| 4 | 50° | NS | 77 (70–80) |
| 12 | 20° | (120–175) | (65–70) |
| 12 | 40° | (125–145) | (70–80) |
| 24 | 20° | 145 (130–170) | ND |
| 24 | 40° | 145 (118–163) | ND |

ND = not determined
NS = not stable

In Table 3, where no range of dissolution time or average dissolution time is stated, none was recorded.

EXAMPLE 2

Effervescent acetylsalicylic acid tablets were produced by direct compression (hardness 7–9 kp) of dry powder mixtures of the following formulations:

| | (A) mg | (B) mg |
|---|---|---|
| Coated ASA | 350 | 350 |
| NaHCO$_3$/Na$_2$CO$_3$ | 460 | 384 |
| Citric acid/tri-sodium citrate mixture | 435 | 261 |
| TAB BASE (spray-crystallized dextrose) | — | 250 |
| Total Weight | 1245 | 1245 |

The initial dissolution times for the tablets are set forth in Table 4 below:

TABLE 4

| Formulation | Average Dissolution Time (range) (Secs) |
|---|---|
| A | 101 (86–115) |
| B | 75 (70–79) |

It will be noted from Table 4 that the addition of spray-crystallized dextrose to replace 250 mg of the effervescent tablet causes a substantial reduction in dissolution time without increasing the weight of the tablet. This reduction is maintained during storage although some increase in dissolution time occurs compared to the initial result. The dissolution times after storage for the time and at the temperature specified are set forth in Table 5 below:

TABLE 5

| Formulation | | Average Dissolution Time | |
|---|---|---|---|
| Time (weeks) | Temperature (°C.) | A (secs) | B (secs) |
| Initially | | 101 (86–115) | 75 (70–79) |
| 2 | 40° | ND | 100 (92–125) |
| 2 | 50° | 203 (183–217) | 92 (88–100) |
| 4 | 20° | ND | 105 (98–115) |
| 4 | 40° | ND | 124 (102–158) |
| 4 | 50° | NS | 107 (105–131) |

NS = not stable
ND = not determined

EXAMPLE 3

Effervescent acetylsalicylic acid tablets were produced by direct compression (hardness 7–9 kp) of dry powder mixtures of the following formulations:

| (A) | Coated ASA | 350 mg |
|---|---|---|
| | $NaHCO_3/Na_2CO_3$ | 460 |
| | Citric acid/tri-sodium citrate mixture | 435 mg |

(B) Formulation A above with addition of 100 mg TAB BASE (spray-crystallized dextrose).
(C) Formulation A above with addition of 200 mg TAB BASE.
(D) Formulation A above with addition of 300 mg TAB BASE.
(E) Formulation A above with addition of 400 mg TAB BASE.

The initial dissolution times for the tablets are set forth in Table 6 below:

TABLE 6

| Formulation | Average Dissolution Time (Secs) |
|---|---|
| A | 101 |
| B | 79 |
| C | 67 |
| D | 79 |
| E | 71 |

It can be seen from Table 6 that the addition of spray crystallized dextrose in amounts between 100 mg and 400 mg substantially reduce the initial dissolution time of the tablets. These tablets were not subjected to testing after storage.

EXAMPLE 4

Effervescent acetylsalicylic acid tablets were produced by direct compression (hardness 7–9 kp) of dry powder mixtures of the following formulations:

| | | (1) | (2) |
|---|---|---|---|
| (A) | Coated ASA | 350 | 350 |
| | $NaHCO_3$ | 435 | 316 |
| | $Na_2CO_3$ | 25 | 100 |
| | Citric acid/tri-sodium citrate mixture | 435 | 435 |

(B) Formula A(2) above with addition of 50 mg TAB BASE (spray crystallized dextrose).
(C) Formula A(2) above with addition of 100 mg TAB BASE.
(D) Formula A(2) above with addition of 150 mg TAB BASE.
(E) Formula A(2) above with addition of 400 mg TAB BASE.

The initial dissolution times for the tablets are set forth in Table 7 below:

TABLE 7

| Formulation | Average Dissolution Time (range) (Secs) |
|---|---|
| A (1) | 101 (86–115) |
| A (2) | 95 |
| B | (85–110) |
| C | (100–110) |
| D | (85–100) |
| E | 81 |

It will be noted from Table 7 that the addition of spray crystallized dextrose in amounts of 150 mg or less per tablet (ie. 11% by weight) had no effect upon the dissolution rate of the effervescent acetylsalicylic acid aspirin tablets in which 25% by weight of the base component is provided by sodium carbonate.

Additional batches of tablets of Formulations A(2) (hardness 7–8 kp) and E (hardness 7–9 kp) were subjected to testing after storage at the time and temperature specified and the results are set forth in Table 8 below:

TABLE 8

| Formulation | | Average Dissolution Time (range) | |
|---|---|---|---|
| Time (weeks) | Temperature (°C.) | A(2) (secs) | E (secs) |
| Initially | | 83 | 81 |
| 2 | 40° | (130–170) | (90–110) |
| 2 | 50° | (135–145) | (105–110) |
| 4 | 20° | (120–140) | (70–80) |
| 4 | 40° | (145–175) | (75–95) |
| 4 | 50° | (130–140) | (90–110) |
| 12 | 20° | (125–140) | (65–75) |
| 12 | 40° | (145–170) | (81–110) |
| 12 | 50° | (120–150) | NS |
| 24 | 20° | 137 (118–178) | 83 (75–96) |
| 24 | 40° | 147 (138–165) | 97 (80–117) |

NS = not stable

When in Table 8 no dissolution range or average is stated, none was recorded.

As can be seen from Table 8, the addition of 400 mg spray crystallized dextrose to Formulation A(2) caused a substantial reduction in dissolution time on storage but this was not apparent initially.

EXAMPLE 5

Effervescent acetylsalicylic acid tablets were produced by direct compression (hardness 8–11 kp) of dry powder mixtures of the following formulations:

|  | (A) mg | (B) mg |
| --- | --- | --- |
| Coated ASA | 1167 | 1167 |
| NaHCO$_3$/Na$_2$CO$_3$ | 1050 | 1050 |
| Citric Acid | 400 | 400 |
| TAB BASE (spray crystallised dextrose) | — | 800 |

The initial dissolution time for the tablets are set forth in Table 9 below:

TABLE 9

| Formulation | Average Dissolution Time (range) (Secs) |
| --- | --- |
| A | 130 (120–140) |
| B | 95 (80–110) |

The tablets were subjected to testing at the time and temperature specified and the results are set forth in Table 10 below:

TABLE 10

| Formulation | A | B |
| --- | --- | --- |
| Time (weeks) | Temperature (°C.) | Average Dissolution Time (range) (Secs) |
| Initially |  | 130 (120–140) | 95 (80–110) |
| 2 | 20° | 130 (120–135) | ND |
| 2 | 40° | (300–360) | 111 (95–140) |
| 4 | 20° | NS | 104 (90–125) |
| 4 | 40° | NS | 119 (115–125) |
| 12 | 20° | NS | 103 (85–125) |
| 12 | 40° | NS | 111 (100–125) |
| 24 | 20° | NS | 102 (95–125) |
| 24 | 40° | NS | 107 (90–130) |
| 52 | 20° | NS | 112 (90–130) |
| 104 | 20° | NS | 123 (120–125) |

ND = not determined
NS = not stable; no additional results were recorded for Formulation A because of poor stability at 40° C.

It can be seen from Table 10 that the incorporation of 800 spray crystallized dextrose caused a substantial reduction in dissolution time which is maintained during storage.

EXAMPLE 6

Effervescent acetylsalicylic acid tablets were produced by direct compression (hardness 5–7 kp) of dry powder mixtures of the following formulations:

|  | (A) mg | (B) mg | (C) mg | (D) mg |
| --- | --- | --- | --- | --- |
| Coated ASA | 350 | 350 | 350 | 350 |
| NaHCO$_3$ | 389 | 580 | 414 | 293 |
| Na$_2$CO$_3$ | 100 | 25 | 24 | 100 |
| Citric Acid | 362 | 362 | 207 | 207 |
| TAB BASE (Spray crystallized dextrose) | — | — | 250 | 295 |
| Total Weight | 1201 | 1245 | 1245 | 1245 |

The initial dissolution times for the tablets are set forth in Table 11 below:

TABLE 11

| Formulation | Average Dissolution Time (range) (Secs) |
| --- | --- |
| A | (95–120) |
| B | 78 |
| C | 53 |

TABLE 11-continued

| Formulation | Average Dissolution Time (range) (Secs) |
| --- | --- |
| D | 92 |

Tablets (hardness 6–9 kp) were subjected to testing for the time and at the temperature specified and the results are set forth in Table 12 below:

TABLE 12

| Formulation | | A | B | C | D |
| --- | --- | --- | --- | --- | --- |
| Time (weeks) | Temperature (°C.) | Average Dissolution Time | | | |
|  |  | (secs) | (secs) | (secs) | (secs) |
| 2 | 50° | (90–110) | ND | ND | ND |
| 4 | 20° | (105–140) | 70 | 59 | 117 |
| 4 | 40° | (95–120) | 94 | 69 | 111 |
| 4 | 50° | NS | ND | ND | ND |
| 12 | 20° | 118 | 85 | 58 | 127 |
| 12 | 40° | 104 | 107 | 67 | 120 |
| 24 | 20° | 120 | 90 | 77 | 147 |
| 24 | 40° | 116 | 106 | 72 | 173 |

NS = not stable
ND = not determined

It can be seen from Table 12 that the addition of spray crystallized dextrose to replace 250 mg of the effervescent couple in an effervescent acetylsalicylic acid tablet in which 5% by weight of the base component is provided by Na$_2$CO$_3$ caused a substantial reduction in dissolution time. This reduction was maintained with storage time.

EXAMPLE 7

Effervescent acetylsalicylic acid tablets were produced by direct compression of dry powder mixtures of the following formulation:

|  | mg |
| --- | --- |
| Coated ASA | 350 |
| NaHCO$_3$ | 439 |
| Na$_2$CO$_3$ | 24 |
| Citric Acid | 240 |
| Saccharide/Sugar Alcohol* | 400 |

*See Table 13 below.

The initial dissolution times for the tables are set forth in Table 13 below:

TABLE 13

|  | Tablet Hardness | |
| --- | --- | --- |
|  | 4–6 kp | 6–8 kp |
|  | Average Dissolution Time (range): | |
| Saccharide/Sugar Alcohol: | (secs) | (secs) |
| None | 100 (90–120) | 179 (165–190) |
| Sorbitol | ND | 82 (75–90) |
| Mannitol | 54 (45–65) | 55 (45–75) |
| Fructose | 139 (120–150) | 194 (180–120) |
| LD Dextrose[1] | 102 (80–120) | 155 (145–170) |
| HD Dextrose[2] | 73 (60–85) | 132 (120–155) |
| TAB BASE | 71 (65–80) | 97 (85–110) |
| Xylitol | 98 (85–105) | 156 (145–165) |
| Sucrose | 74 (65–80) | 110 (90–135) |
| Lactose | 115 (105–125) | 151 (135–170) |
| Beta-Cyclodextrin | 98 (90–115)* | ND |
| TAB FINE D97HS[3] | 83 (75–90) | 106 (100–115) |
| SWEETREX[4] | 95 (85–105) | 137 (120–160) |
| ROYAL T DEXTROSE[5] | 69 (65–75) | 90 (70–120) |
| TAB FINE S1001[6] | 84 (75–90) | 118 (115–130) |

TABLE 13-continued

| | Tablet Hardness | |
|---|---|---|
| | 4-6 kp | 6-8 kp |
| | Average Dissolution Time (range): | |
| Saccharide/Sugar Alcohol: | (secs) | (secs) |
| TAB FINE F94M[7] | 107 (95-115) | 152 (140-170) |

ND = not determined
* = foaming present
[1]LD Dextrose has a bulk density of 0.71 g/ml and a tapped density of 0.85 g/ml.
[2]HD Dextrose has a bulk density of 0.81 g/ml and a tapped density of 1.04 g/ml.
[3]TAB FINE D97HS is a Trade Mark for an agglomerated dextrose containing 97% dextrose and 3% hydrogenated starch syrup (bulk density 0.68 g/ml; tapped density 0.80 g/ml).
[4]SWEETREX is a Trade Mark for a product containing 68.72% dextrose, 28-33% fructose, 1-2% maltose and 5.7% higher saccharides.
[5]ROYAL T DEXTROSE is a Trade Mark for agglomerated dextrose containing dextrose (94% equivalent) and maltodextrin (82% hexasaccharide, 4% disaccharide and 1% monosaccharide) (bulk density 0.69 g/ml; tapped density 0.89 g/ml).
[6]TAB FINE S100I is a Trade Mark for a product containing 97% sucrose and 3% invert sugar.
[7]TAB FINE F94M is a Trade Mark for a product containing 93% fructose and 7% maltose syrup.

The tablets were subjected to testing for 12 weeks at 20° C. and 40° C. and the results are set forth in Table 14 below:

TABLE 14

| | Tablet Hardness | | | |
|---|---|---|---|---|
| | 4-6 kp | | 6-8 kp | |
| | Average Dissolution Time: | | | |
| | (secs) | | (secs) | |
| Saccharide/Sugar | Temperature | | | |
| Alcohol: | 20° C. | 40° C. | 20° C. | 40° C. |
| None | 141 | 107 | 247 | 193 |
| Sorbitol | ND | ND | 94 | NS |
| Mannitol | 78 | 72 | 89 | 80 |
| Fructose | 158 | 126 | 216 | 175 |
| LD Dextrose[1] | 109 | 91 | 152 | 111 |
| HD Dextrose[2] | 80 | 75 | 121 | 116 |
| TAB BASE | 83 | 85 | 108 | 99 |
| Xylitol | 113 | NS | 183 | NS |
| Sucrose | 90 | 81 | 134 | 97 |
| Lactose | 144 | 138 | 165 | 164 |
| Beta-Cyclodextrin | (125-135)* | (145-165)* | ND | ND |
| TAB FINE D97HS[3] | 87 | 70 | 114 | 87 |
| SWEETREX[4] | 108 | 101 | 159 | 139 |
| ROYAL T DEXTROSE[5] | 74 | 70 | 104 | 90 |
| TAB FINE S100I[6] | 89 | 79 | 134 | 102 |
| TAB FINE F94M[7] | 119 | 103 | 177 | 131 |

ND = not determined
NS = not stable
* = foaming present

Comparing against base formulation containing zero saccharide, the following observations were made:

SORBITOL

The inclusion of 400 mg sorbitol results in faster dissolution initially and after 40° C. and 20° C. storage at 6 to 8 kp hardness range, but has poor stability at 40° C. after 4 weeks. Tablets could not be prepared at 4 to 6 kp hardness range.

MANNITOL

The inclusion of 400 mg mannitol results in faster dissolution initially and after 40° C. and 20° C. storage for both hardness ranges. However, the increase in dissolution times after 40° C. storage is not as significant as that seen previously in Example 1E. Tablets containing 400 mg mannitol at both hardness ranges were friable, easily abraded and had considerable surface picking problems. In order to improve these tablet characteristics, a higher compression force, and thus an increased hardness, is required with a resultant increase in dissolution time.

FRUCTOSE AND FRUCTOSE VARIANTS

The inclusion of 400 mg and 700 mg fructose results in slower dissolution initially and after 40° C. and 20° C. storage for both hardness ranges. The inclusion of 400 mg agglomerated fructose (Tab Fine F94M) results in slightly faster dissolution than 400 mg fructose at similar conditions. The inclusion of 400 mg Sweetrex (40% fructose) causes a further reduction in dissolution time at similar conditions but is slower than mannitol or sorbitol.

XYLITOL

The inclusion of 400 mg xylitol results in similar dissolution initially at 4 to 6 kp hardness range and faster dissolution at 6 to 8 kp. Faster dissolution occurs after 20° C. storage for both hardness ranges, but tablets containing xylitol showed poor stability after 1 week storage at 40° C.

LACTOSE

The inclusion of 400 mg lactose (anhydrous) resulted in slower dissolution initially at the 4 to 6 kp hardness range but faster dissolution initially at the 6 to 8 kp range. Similar dissolution occurs after 40° C. and 20° C. storage at the 4 to 6 kp hardness range. Faster dissolution occurs after 40° C. and 20° C. for the 6 to 8 kp range. Dissolution times were slower than those seen with sorbitol or mannitol.

BETA-CYCLODEXTRIN

The inclusion of 400 mg beta-cyclodextrin resulted in faster dissolution initially and after 40° C. and 20° C. storage but has undesirable foaming present after dissolution. Tablets could not be prepared at 6 to 8 kp hardness range due to compression difficulties.

INOSITOL

Tablets containing 400 mg inositol could not be prepared due to compression difficulties.

SUCROSE AND SUCROSE VARIANTS

The inclusion of 400 mg sucrose results in faster dissolution initially and after 40° C. and 20° C. storage for both hardness ranges. Dissolution times were slower than those seen with mannitol or sorbitol. The inclusion of 400 mg agglomerated sucrose (Tab Fine S100I) results in slightly slower dissolution times than sucrose at similar conditions. Tab Fine S100I contains invert sugars, which is in part fructose, and hence the increase in dissolution time compared with sucrose.

DEXTROSE AND DEXTROSE VARIANTS

The inclusion of 400 mg dextrose or dextrose variants results in faster dissolution initially and after 40° C. and 20° C. storage at both hardness ranges.

Low density dextrose has slower dissolution times compared to high density dextrose and other dextrose variants (Tab Base, Tab Fine D97HS and Royal T Dextrose) initially and after 40° C. and 20° C. storage at both hardness ranges. This difference is due to higher force required to compress the low density dextrose at comparable hardness range.

High density dextrose has similar dissolution times to the dextrose variants when compressed between 4 to 6 kp hardness. When compressed between 6 to 8 kp hardness, high density dextrose has slower dissolution than the dextrose variants initially and after 40° C. and 20° C. storage. For both low density and high density dextrose, compression was difficult at the 6 to 8 kp hardness range; tablets were on the verge of capping.

Of the dextrose variants tested, Tab Fine D97HS has slower dissolution than Tab Base and Royal T Dextrose initially at both hardness ranges. At 40° C. storage Tab Fine D97HS dissolution times decrease slightly to be similar to Royal T Dextrose. Dissolution times remain similar to the initial at 20° C. storage.

Royal T dextrose is slightly faster than Tab Base, both initially and on storage at 40° C. and 20° C. at both hardness ranges. Only the Mannitol variant dissolves faster than Royal T Dextrose. Tablets containing Royal T Dextrose were slightly more susceptible to abrasion than those containing Tab Base.

EXAMPLE 8

Effervescent acetylsalicylic acid tablets were produced by direct compression of dry powder mixtures of the following formulation:

|  | mg |
|---|---|
| Coated ASA | 350 |
| NaHCO₃ | 439 |
| Na₂CO₃ | 24 |
| Citric Acid | 240 |
| TAB BASE* | 0–700 mg |

*See Table 15 below.

The initial dissolution times for the tablets are set forth in Table 15 below.

TABLE 15

| | Tablet Hardness | |
|---|---|---|
| | 4–6 kp | 6–8 kp |
| TAB BASE: | Average Dissolution Time (range): | |
| (mg) | (secs) | (secs) |
| 0 | 100 (90–120) | 179 (165–190) |
| 50 | 100 (90–120) | 132 (115–150) |
| 100 | 81 (70–100) | 100 (90–110) |
| 200 | 72 (65–80) | 94 (85–100) |
| 300 | 75 (60–90) | 90 (80–100) |
| 400 | 71 (65–80) | 97 (85–110) |
| 500 | 77 (65–90) | 95 (85–105) |
| 600 | 74 (60–85) | 88 (85–90) |
| 700 | 104 (95–120)* | 79 (70–90) |

* = tablets float

The tablets were subjected to testing for 12 weeks at 20° C. and 40° C. and the results are set forth in Table 16 below:

TABLE 16

| | Tablet Hardness | | | |
|---|---|---|---|---|
| | 4–6 kp | | 6–8 kp | |
| | Temperature | | | |
| | 20° C. | 40° C. | 20° C. | 40° C. |
| TAB BASE: | Average Dissolution Time: | | | |
| (mg) | (secs) | (secs) | (secs) | (secs) |
| 0 | 141 | 107 | 247 | 193 |
| 50 | 115 | 95 | 168 | 121 |
| 100 | 92 | 78 | 126 | 95 |
| 200 | 89 | 74 | 112 | 81 |
| 300 | 87 | 73 | 104 | 79 |
| 400 | 83 | 85 | 108 | 99 |
| 500 | 86 | 69 | 106 | 87 |
| 600 | 82 | 83 | 95 | 71 |

TABLE 16-continued

| | Tablet Hardness | | | |
|---|---|---|---|---|
| | 4–6 kp | | 6–8 kp | |
| | Temperature | | | |
| | 20° C. | 40° C. | 20° C. | 40° C. |
| TAB BASE: | Average Dissolution Time: | | | |
| (mg) | (secs) | (secs) | (secs) | (secs) |
| 700 | 113* | 86* | 88 | 68 |

* = tablets float

At 12 weeks the 400 mg TAB BASE tablets had an average dissolution time of (a) 83 secs (20° C.) and 85 secs (40° C.) for the 4–6 kp tablets and 108 secs (20° C.) and 99 secs (40° C.) for the 6–8 kp tablets compared with (a) 141 secs (20° C.) and 107 secs (40° C.) and (b) 247 secs (20° C.) and 193 secs (40° C.) respectively for the tablets not containing TAB BASE.

EXAMPLE 9

Example 8 was repeated using sucrose instead of TAB BASE and the results obtained are set forth in Table 17 and 18 (8 weeks stability) below:

TABLE 17

| | Tablet Hardness | |
|---|---|---|
| | 4–6 kp | 6–8 kp |
| SUCROSE: | Average Dissolution Time (range): | |
| (mg) | (secs) | (secs) |
| 0 | 100 (90–120) | 179 (165–190) |
| 100 | 104 (95–110) | ND |
| 200 | 100 (90–110) | 151 (140–160) |
| 300 | 87 (75–105) | 116 (105–130) |
| 400 | 74 (65–80) | 110 (90–135) |
| 500 | 89 (85–95) | 117 (100–140) |
| 600 | 74 (65–85) | 112 (105–120) |
| 700 | 77 (70–85) | 126 (120–130) |

ND = not determined

TABLE 18

| | Tablet Hardness | | | |
|---|---|---|---|---|
| | 4–6 kp | | 6–8 kp | |
| | Temperature | | | |
| | 20° C. | 40° C. | 20° C. | 40° C. |
| SUCROSE: | Average Dissolution Time | | | |
| (mg) | (secs) | (secs) | (secs) | (secs) |
| 0 | 136 | 121 | 260 | 208 |
| 100 | 133 | 111 | ND | ND |
| 200 | 115 | 85 | 159 | 114 |
| 300 | 98 | 82 | 130 | 100 |
| 400 | 90 | 79 | 116 | 98 |
| 500 | 97 | 84 | 135 | 105 |
| 600 | 87 | 77 | 126 | 105 |
| 700 | 90 | 79 | 138 | 120 |

ND = not determined

At 12 weeks the 400 mg Sucrose tablets had an average dissolution time of (a) 90 secs (20° C.) and 81 secs (40° C.) for the 4–6 kp tablet and (b) 134 secs (20° C.) and 97 secs (40° C.) for the 6–8 kp tablet compared with (a) 141 secs (20° C.) and 107 secs (40° C.) and (b) 247 secs (20° C.) and 193 secs (40° C.) respectively for the 0 mg sucrose tablets.

EXAMPLE 10

Effervescent acetylsalicylic acid tablets (5 to 7 kp hardness) were produced by direct compression of dry powder mixtures of the following formulations:

|  | (A) mg | (B) mg | (C) mg |
|---|---|---|---|
| Coated ASA | 350 | 350 | 350 |
| $KHCO_3/K_2CO_3$ | 572 | 525 | 525 |
| Citric Acid | 323 | 207 | 207 |
| Spray Crystallized Dextrose (TAB BASE) | — | 163 | 400 |
| Tablet Weight | 1245 | 1245 | 1482 |

The initial dissolution times for the tablets are set forth in Table 19 below:

TABLE 19

| Formulation | Average Dissolution Time (range) (sec) |
|---|---|
| A | 206 (200–215) |
| B | 131 (90–152) |
| C | 107 (60–130) |

It can be seen from Table 19 that the addition of spray crystallized dextrose to replace 163 mg of the effervescent tablet caused a substantial reduction in dissolution time without increasing the weight of the tablet. Increasing the amount of spray crystallized dextrose to 400 mg again substantially reduced the initial dissolution times of the tablets. These tablets were not subjected to testing after storage.

We claim:

1. An effervescent acetylsalicylic acid tablet adapted to disintegrate or dissolve rapidly on addition to water, the tablet obtained by direct compression of a directly compressible dry powder mixture containing acetylsalicylic acid in the form of particles coated with a water-soluble coating material having a melting point of at least 105° C. and selected from the group consisting of low-molecular weight amino acids, sugars, sugar alcohols and mixtures thereof, and an effervescent couple, said mixture being admixed with a powdered binder selected from the group consisting of dextrose, sucrose and mixtures thereof in an amount sufficient to increase the rate of disintegration, dissolution or both of the tablet compared with said directly compressed dry powder mixture, said binder being present in an amount of 10 to 40% by weight based upon the combined weights of the other components of said dry powder mixture.

2. A tablet as claimed in claim 1, wherein the said amount is 15 to 30% by weight based upon the combined weights of the other components of the dry powder mixture.

3. A tablet as claimed in claim 1, wherein the said binder is dextrose.

4. A tablet as claimed in claim 3, wherein the dextrose is in the form of a dextrate.

5. A tablet as claimed in claim 1, wherein the said binder is in spray-crystallized form.

6. A tablet as claimed in claim 1, wherein the dry powder mixture consists in addition to said binder, essentially of acetylsalicylic acid, sodium bicarbonate and citric acid.

7. A tablet as claimed in claim 1, wherein the base component of the effervescent couple is a mixture of sodium bicarbonate and sodium carbonate; said sodium carbonate comprising 5 to 25% by weight of said base component.

* * * * *